(12) United States Patent
Koulikov et al.

(10) Patent No.: US 8,659,758 B2
(45) Date of Patent: Feb. 25, 2014

(54) LASER BASED CAVITY ENHANCED OPTICAL ABSORPTION GAS ANALYZER WITH LASER FEEDBACK OPTIMIZATION

(75) Inventors: Serguei Koulikov, Mountain View, CA (US); Alexander Kachanov, San Jose, CA (US)

(73) Assignee: Li-Cor, Inc., Lincoln, NE (US)

( * ) Notice: Subject to any disclaimer, the term of this patent is extended or adjusted under 35 U.S.C. 154(b) by 178 days.

(21) Appl. No.: 13/252,915

(22) Filed: Oct. 4, 2011

(65) Prior Publication Data

US 2013/0083328 A1  Apr. 4, 2013

(51) Int. Cl.
*G01N 21/00* (2006.01)
*G01N 21/85* (2006.01)

(52) U.S. Cl.
CPC ................... *G01N 21/8507* (2013.01)
USPC .......................... 356/436; 356/437

(58) Field of Classification Search
CPC ................ G01N 21/00; G01N 21/8507
USPC .................................. 356/432–444
See application file for complete search history.

(56) References Cited

U.S. PATENT DOCUMENTS

| | | |
|---|---|---|
| 3,938,365 A | 2/1976 | Dewey |
| 4,793,709 A | 12/1988 | Jabr et al. |
| 5,432,610 A | 7/1995 | King et al. |
| 5,528,040 A | 6/1996 | Lehmann et al. |
| 5,544,186 A | 8/1996 | Sauer et al. |
| 5,912,740 A | 6/1999 | Zare et al. |
| 5,929,981 A | 7/1999 | Keilbach |
| 5,973,864 A | 10/1999 | Lehmann et al. |
| 6,084,682 A | 7/2000 | Zare et al. |
| 6,466,322 B1 | 10/2002 | Paldus et al. |
| 6,504,145 B1 | 1/2003 | Romanini et al. |
| 6,608,683 B1 | 8/2003 | Pilgrim et al. |
| 6,618,148 B1 | 9/2003 | Pilgrim et al. |
| 7,012,696 B2 | 3/2006 | Orr et al. |

(Continued)

FOREIGN PATENT DOCUMENTS

| | | |
|---|---|---|
| JP | 07-270308 A | 10/1995 |
| WO | WO 2007/004168 A1 | 1/2007 |
| WO | WO 2008/026189 A1 | 3/2008 |

OTHER PUBLICATIONS

International Search Report and Written Opinion for PCT/US2011/049453 dated Mar. 23, 2012.

(Continued)

*Primary Examiner* — Michael P Stafira
(74) *Attorney, Agent, or Firm* — Gerald T. Gray; Leydig, Voit & Mayer LLP

(57) ABSTRACT

Optical feedback assisted cavity enhanced absorption spectroscopy systems and methods for measuring trace gases with improved long-term stability and reproducibility include a laser coupled with a resonant optical cavity containing a gaseous medium and having at least two cavity mirrors and a plurality of optical resonance cavity modes. The laser emits continuous wave laser light with a mean optical frequency of the laser being adjustable over a range of frequencies, and the laser is responsive to optical feedback light emerging from the cavity. The transmissivity of at least one of the cavity mirrors is selected such that the intensity of the optical feedback light impinging on the laser is below a threshold intensity value so as to ensure that a frequency hold interval range of the optical frequency of the laser is smaller than a free spectral range of the cavity.

30 Claims, 7 Drawing Sheets

1 – source of continuous wave laser light
2 – optical system for directing laser light from to the optical cavity
3 – beam-splitter
4 – resonant optical cavity
5, 6, and 7 – cavity mirrors
8 – photo-detector for measuring the intensity of the incident onto the cavity light
9 – photo-detector for measuring the intensity of the circulated intra-cavity optical power

(56) References Cited

U.S. PATENT DOCUMENTS

| | | |
|---|---|---|
| 7,069,769 B2 | 7/2006 | Kung |
| 7,245,380 B2 | 7/2007 | Kosterev |
| 7,259,856 B2 | 8/2007 | Kachanov et al. |
| 7,263,871 B2 | 9/2007 | Selker et al. |
| 7,398,672 B2 | 7/2008 | Riddle |
| 7,450,240 B2 | 11/2008 | Morville et al. |
| 7,569,823 B2 | 8/2009 | Miller |
| 7,612,885 B2 | 11/2009 | Cole et al. |
| 7,663,756 B2 | 2/2010 | Cole |
| 7,679,750 B2 | 3/2010 | Li et al. |
| 7,765,871 B2 | 8/2010 | Riddle |
| 7,805,980 B2 | 10/2010 | Kosterev |
| 7,902,534 B2 | 3/2011 | Cole et al. |
| 2003/0189711 A1* | 10/2003 | Orr et al. ............ 356/484 |
| 2004/0065816 A1 | 4/2004 | Ye et al. |
| 2006/0084180 A1 | 4/2006 | Paldus et al. |
| 2006/0119851 A1 | 6/2006 | Bounaix |
| 2006/0123884 A1 | 6/2006 | Selker et al. |
| 2006/0181710 A1* | 8/2006 | Kachanov et al. ....... 356/437 |
| 2008/0134756 A1 | 6/2008 | Riddle |
| 2008/0151248 A1 | 6/2008 | Cole et al. |
| 2008/0196477 A1 | 8/2008 | Van Herpen |
| 2009/0229345 A1 | 9/2009 | Van Kesteren |
| 2009/0249861 A1 | 10/2009 | Van Dijk et al. |
| 2009/0288474 A1 | 11/2009 | Kalkman et al. |
| 2010/0002234 A1 | 1/2010 | Cormier et al. |
| 2010/0011836 A1 | 1/2010 | Kalkman et al. |
| 2010/0296095 A1 | 11/2010 | Hong et al. |
| 2011/0214479 A1 | 9/2011 | Kachanov et al. |
| 2011/0295140 A1 | 12/2011 | Zaidi et al. |
| 2013/0050706 A1 | 2/2013 | Koulikov et al. |

OTHER PUBLICATIONS

International Search Report and Written Opinion for PCT/US2011/026922 dated Apr. 27, 2011.

Burggraf et al., "Quantitative Photoacoustic Spectroscopy of Intensely Light-Scattering Thermally Thick Samples," Anal. Chem., 1981, vol. 53, pp. 759-764.

Hippler et al., "Cavity-enhanced resonant photoacoustic spectroscopy with optical feedback cw diode lasers: A novel technique for ultratrace gas analysis and high-resolution spectroscopy," The Journal of Chemical Physics, 2010, vol. 133, pp. 044308-1-044308-8.

Cermak, Peter et al., "Optical-Feedback Cavity-Enhanced Absorption Spectroscopy Using a Short-Cavity Vertical-External-Cavity Surface-Emitting Laser," IEEE Photonics Technology Letters, IEEE Service Center, Piscataway, NJ, US, (2010), vol. 22, No. 21, pp. 1607-1609.

Clairon, A. et al., "Frequency Noise Analysis of Optically Self-Locked Diode Lasers," IEEE J. Quantum Electronics, 25(6):1131-1142 (1989).

Courtillot, I. et al., "Sub-ppb $NO_2$ detection by optical feedback cavity-enhanced absorption spectroscopy with a blue diode laser," Applied Physics B, (2006), vol. 85, No. 2-3, pp. 407-412.

Crosson, Eric R. et al., "Stable Isotope Ratios Using Cavity Ring-Down Spectroscopy: Determination of 13C/12C for Carbon Dioxide in Human Breath," Analytical Chemistry, May 1, 2002, vol. 74, No. 9, pp. 2003-2007.

Hamilton, D. J. et al., "A quantum cascade laser-based optical feedback cavity-enhanced absorption spectrometer for the simultaneous measurement of $CH_4$ and $N_2O$ in air," Applied Physics B, (2011), vol. 102, No. 4, pp. 879-890.

Kosterev, A. A. et al., "Quartz-enhanced photoacoustic spectroscopy," Optics Letters 27(21):1902-1904 (Nov. 1, 2002).

Kosterev, A. A. et al., "Trace Humidity Sensor based on Quartz-Enhanced Photoacoustic Spectroscopy," LACSEA 2006, Incline Village, NV, Feb. 5-9, 2006.

Morville, J. et al., "Trace gas detection with DFB lasers and cavity ring-down spectroscopy," SPIE Proc., (2002), vol. 4485, pp. 236-243.

Morville, J. et al., "Effects of laser phase noise on the injection of a high-finesse cavity," Applied Optics, (2002), vol. 41, No. 33, pp. 6980-6990.

Morville, J. et al., "Two schemes for trace detection using cavity ringdown spectroscopy," Applied Physics B, (2004), vol. 78, pp. 465-476.

Morville, J. et al., "Fast, low-noise, mode-by-mode, cavity-enhanced absorption spectroscopy by diode-laser self-locking," Applied Physics B, (2005), vol. 80, No. 8, pp. 1027-1038.

Motto-Ros, V. et al., "Extensive characterization of optical feedback cavity enhanced absorption spectroscopy (OF-CEAS) technique: ringdown-time calibration of the absorption scale," Applied Physics B, (2008), vol. 91, No. 1, pp. 203-211.

Romani, D. et al., "CW cavity ring down spectroscopy," Chemical Physics Letters, (1997), 264, pp. 316-322.

Romani, D. et al., "Diode laser cavity ring down spectroscopy," Chemical Physics Letters, (1997), 270, pp. 538-545.

Romani, D. et al., "Measurement of trace gases by diode laser cavity ringdown spectroscopy," Proc. SPIE EUROPTO (Ser. Environmental Sensing), (1999), vol. 3821, pp. 94-104.

Rossi, A. et al., "Optical enhancement of diode laser-photoacoustic trace gas detection by means of external Fabry-Perot cavity," Appl. Phys. Lett. 87, 041110 (2005).

Wehr, R. et al., "Optical feedback cavity-enhanced absorption spectroscopy for in situ measurements of the ratio 13C: 12C in CO2," Applied Physics B, (2008), vol. 92, No. 3, pp. 459-465.

European Search Report for EP Patent Application No. 12275155.5 dated Feb. 22, 2013.

* cited by examiner

1 – source of continuous wave laser light
2 – optical system for directing laser light from to the optical cavity
3 – beam-splitter
4 – resonant optical cavity
5, 6, and 7 – cavity mirrors
8 – photo-detector for measuring the intensity of the incident onto the cavity light
9 – photo-detector for measuring the intensity of the circulated intra-cavity optical power If the laser is rotated by angle of $\alpha$, the intracavity power is ~ $\cos(\alpha)$, the intensity of the light directed to the laser is also ~ $\cos(\alpha)$, and the intensity of the feedback light coupled to the laser is ~ $\cos^2(\alpha)$. There is no attenuator between the laser and the cavity. Their mutual orientation affects the laser-cavity coupling rate.

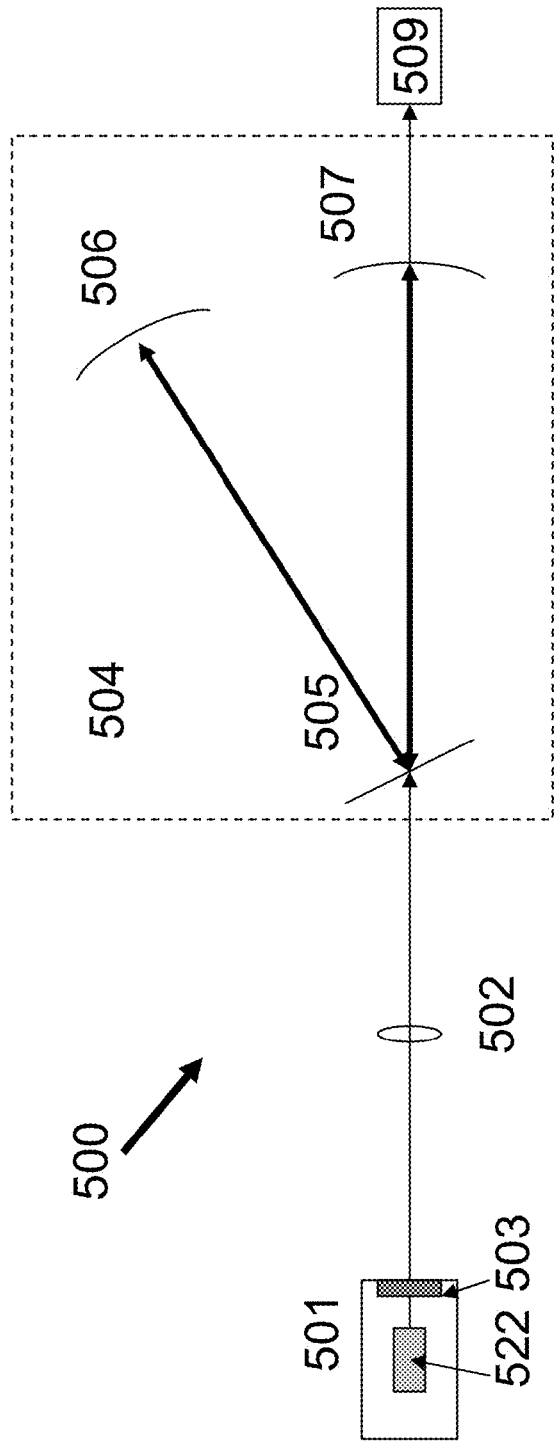

501 – source of continuous wave laser light
522 – active laser medium
503 – output laser coupler
502 – optical system for directing the laser light from the laser to the optical cavity
504 – resonant optical cavity
505, 506 and 507 – cavity mirrors
509 - photo-detector for measuring the intensity of the circulated intra-cavity optical power by measuring the intensity of the light transmitted by the optical cavity

FIG. 5

601 – source of continuous wave laser light
602 – optical system for directing the laser light from the laser to the optical cavity
604 – resonant optical cavity
605, 606 and 607 – cavity mirrors
609 - photo-detector for measuring the intensity of the circulated intra-cavity optical power by measuring the intensity of the light transmitted by the optical cavity
608 – acoustic sensor The purpose of the double (or multiple) stage optical isolators is to completely block the light, which travels in the opposite direction.
LD – laser diode, PD – photodiode, BS – beam splitter, $BS_1 \sim 50:50$, $BS_2 > 90\%$ in transmission.
Selection of $R_1$, $R_2$ and $R_3$ defines the optical feedback intensity

LASER BASED CAVITY ENHANCED OPTICAL ABSORPTION GAS ANALYZER WITH LASER FEEDBACK OPTIMIZATION

BACKGROUND

The present invention relates generally to generally to trace gas detection and more specifically to cavity enhanced absorption spectroscopy (CEAS) systems and methods for measuring the trace gases.

In cavity enhanced optical absorption spectroscopy systems and methods, radiation of a laser is directed into a resonance cavity, and the optical intensity inside the cavity is observed. The optical frequency of the laser can be periodically scanned. If it is assumed for clarity that the laser linewidth is much smaller than the cavity resonance width, at the moment when the laser light frequency coincides with a cavity mode transmission peak the optical intensity inside the resonance cavity reflects total cavity loss, and the total cavity loss can be quantitatively determined provided that the incident intensity and cavity parameters are known. The total cavity loss is a sum of the cavity mirror losses and losses caused by absorption of a gas mixture present in the cavity. The lower the cavity mirror losses, or equivalently, the higher each mirror's reflectivity—the smaller the absorption of the intra-cavity gas mixture that can be detected. With very high reflectivity mirrors, the laser linewidth will become too large compared to the cavity resonance width, thus limiting achievable enhancement of the gas mixture absorption by the cavity. This can be helped by narrowing the laser linewidth using optical feedback from the cavity and a laser that is sensitive or responsive to optical feedback from the cavity. With such a laser during the scan, as the frequency of the laser light approaches the frequency of one of the cavity modes, the laser locks to that mode. By saying that the laser is locked to the mode it is meant that the laser linewidth becomes much smaller than the resonance mode width, and that regardless whether the frequency scan range of the unlocked laser may be large, in a locked condition the optical frequency of the laser will change only within the resonance peak. As the laser frequency scan continues, the laser will lose the lock to the current cavity mode and relock to the next cavity mode that it approaches. Due to the optical feedback effect, the laser optical frequency during the scan will essentially take the number of discrete values corresponding to the peaks of the cavity mode resonances that are equidistant in optical frequency. A discrete absorption spectrum of the analyzed gas can thus be obtained by sequential coupling to the entire set of the cavity modes within the scan range, and the trace gas concentration can be derived from the absorption spectrum. This sub-family of cavity enhanced optical absorption spectroscopy systems and methods that uses optical feedback will be referred to as optical feedback cavity enhanced absorption spectroscopy (OF CEAS).

In OF CEAS, the strength of the optical feedback from the resonance cavity to the laser has to be in certain limits, otherwise it is impossible to provide reproducible scan-to-scan mode coupling as the laser scans. In OF CEAS systems and methods that are known so far, complex optical components are used for this purpose, such as Faraday isolators, variable optical attenuators, or polarization rotators. Adverse interference effects, temperature drifts and aging drifts may result from these components in the system. Achieving high stability and high reproducibility of the optical absorption measurements becomes a major problem.

Therefore it is desirable to provide OF CEAS systems and methods that overcome the above and other problems. In particular, very high stability and reproducibility of the absorption measurements should be achieved while retaining reproducible scan to scan sequential coupling to every mode in the cavity with no modes missing.

BRIEF SUMMARY

The present invention provides optical feedback assisted cavity enhanced absorption spectroscopy systems and methods for measuring trace gases with improved long-term stability and reproducibility.

Embodiments of the present invention advantageously enable achieving a laser frequency scan across cavity modes without missing any of the cavity many modes while providing the measurement of optical absorption of the intra-cavity gas mixture with no additional optical elements in the path between the laser and the cavity dedicated to control the optical feedback strength. In prior systems, additional optical components are used to help ensure that no such modes may be missed. In the present embodiments, the laser can be reproducibly locked to any optical resonance cavity mode within the laser's adjustable frequency range, without the added complexity present in prior systems, and more importantly without the instability and the perturbations caused by such additional elements.

In order to reduce complexity and obtain sequential coupling, e.g., when the optical locking range is not larger than the cavity FSR (free spectral range), the optical feedback strength is kept below a threshold value,. In certain embodiments, this is accomplished by one of three different approaches, e.g., by one of approaches 1) or 2) below, or 3) their combination:

1) For the first approach, the total round-trip loss of the cavity is chosen to provide desirable instrument sensitivity, whereas the transmission or transmissivity of the mirror from which the feedback light emerges from the cavity is selected or set to provide optical feedback strength below a threshold value.

2) For the second approach, in case of using a laser that has intrinsic linearly polarized output emission and a cavity having two sets of linearly polarized modes orthogonal to each other, the laser is oriented in such a way that its output polarization makes a non-zero angle to orthogonally polarized cavity mode sets. The angle value is set to provide optical feedback strength for each set of modes below the threshold value.

In certain embodiments, e.g., if it turns out that the optical feedback strength is above the threshold value in the entire range of mutual orientation angle between the laser and the cavity eigenpolarizations, the second approach is combined with the first approach, namely the transmission of the coupling mirror is set to provide optical feedback strength below the threshold for both mode sets. When there is non-zero angle between the laser light and cavity mode polarizations, the laser can be locked to two sets of the orthogonally polarized cavity modes. The mode losses for two different polarizations are different and fixed by the design of the mirror coatings, e.g., multi-layer mirror coatings.

This second approach provides several additional advantages, for example:
   the loss difference between orthogonally polarized modes can be used as an internal standard in cavity enhanced absorption measurements;
   same loss difference between orthogonally polarized mode sets provides wider dynamic range with weaker spectral lines being measured using a lower loss mode set while strong spectral lines may be saturated, but the strong spectral lines will then be measured using a higher loss mode set;

the existing difference of the mode frequencies between the orthogonally polarized mode sets results in higher spectral resolution.

In certain embodiments, systems and methods are provided for detecting trace gases using a resonance optical cavity, containing a gas mixture, that has two or more mirrors and that is capable of being frequency-scanned by changing the optical length of the cavity. A laser or other light source that is capable of being frequency-scanned is coupled to the cavity though one of the cavity mirror, e.g., a "coupling mirror". When the frequency of the laser light approaches the frequency of one of the cavity modes, the laser begins to fill the cavity to that mode. Optical intensity inside the resonance cavity reflects total cavity loss at the moment when the laser light frequency coincides with the cavity mode transmission peak. The total cavity loss is a sum of the cavity mirror losses and losses caused by absorption of the analyzed gas mixture. Control of the feedback intensity of the light incident from the cavity to the laser enables reproducible locking to any optical resonance cavity mode within the adjustable frequency range of the laser.

According to one aspect of the present invention, a system is provided for detecting one or more analyte species present in a gaseous or liquid medium. The system typically includes a resonant optical cavity containing said medium and having at least two cavity mirrors, one of which is a cavity coupling mirror, with the cavity having a plurality of optical resonance cavity modes, and a laser that emits continuous wave laser light, wherein the laser is capable of being scanned whereby a mean optical frequency of the laser is adjustable over a range of frequencies, and wherein the laser is responsive to optical feedback light emerging from the cavity. The system also typically includes mode matching optics configured to couple the laser light to the cavity via the cavity coupling mirror, and a detector configured to measure an intensity of the intracavity optical power of light circulating in the cavity and to generate a signal representing the intracavity optical power of light circulating in the cavity. The cavity is typically designed wherein the transmissivities of the at least two cavity mirrors are selected or set such that the intensity of the optical feedback light impinging on the laser is below a threshold intensity value so as to ensure that a frequency hold interval range of the optical frequency of the laser is smaller than a free spectral range of the cavity. For example, to advantageously avoid using a separate optical feedback strength adjustment element, the transmissivity (i.e., a metric indicative of the amount of light passing from the cavity through a mirror) of all mirrors, and in particular of the mirror through which the feedback light comes back to the laser, is selected such that the optical feedback strength to the laser is below the threshold value. This usually means that the transmissivity of the mirror providing feedback to the laser should be much lower than that of the other mirrors. For example, to advantageously bring the system to the same enhancement as a system having three mirrors with the same reflectivities and including a separate optical feedback strength adjustment element (called for this example "system 1"), the cavity roundtrip loss can be made equal to that of the cavity of system 1 (but without using such adjustment element); the loss factor of the cavity roundtrip is sum of natural logarithms of the cavity mirrors reflectivities, so one can make the two cavities equal by choosing $4*\ln(R)=\ln(R1)+2*\ln(R2)+\ln(R3)$ where R is relectivity of the mirrors of system 1, and for the V-cavity embodiment, R1 is reflectivity of one end mirror, R2 is the reflectivity of the coupling mirror (providing feedback to the laser), and R3 is the reflectivity of the other end mirror.

According to another aspect of the present invention, a system is provided for detecting one or more analyte species present in a gaseous or liquid medium. The system typically includes a resonant optical cavity containing the medium and having at least two cavity mirrors, one of which is a cavity coupling mirror, with the cavity having a plurality of optical resonance cavity modes, wherein the cavity has two sets of linearly polarized cavity modes orthogonal to each other, and a laser that emits continuous wave laser light, wherein the laser has a linearly polarized output, wherein the laser is capable of being scanned whereby a mean optical frequency of the laser is adjustable over a range of frequencies, and wherein the laser is responsive to optical feedback light emerging from the cavity. The system also typically includes mode matching optics configured to couple the laser light to the cavity via the cavity coupling mirror, and a detector configured to measure an intensity of the intracavity optical power of light circulating in the cavity and to generate a signal representing the intracavity optical power of light circulating in the cavity. In one embodiment, an orientation of the laser relative to the cavity is selected so that the output polarization of the laser makes a non-zero angle with respect to the polarization of the cavity modes so that the intensity of the optical feedback light impinging on the laser is below a threshold intensity value so as to ensure locking to one or more of the plurality of optical resonance cavity modes that have a frequency within said range of frequencies of the laser. In certain aspects, the orientation of the laser relative to the cavity is adjustable so that the output polarization of the laser makes a non-zero angle with respect to the polarization of the cavity modes so that the intensity of the optical feedback light impinging on the laser is below the threshold intensity value. In certain aspects, the system includes a means for adjusting the laser position and/or orientation so as to adjust the angle of the output polarization with respect to the polarization of the cavity modes.

According to yet another aspect of the present invention, a system is provided for detecting one or more analyte species present in a gaseous or liquid medium. The system typically includes a resonant optical cavity containing the medium and having at least two cavity mirrors, one of which is a cavity coupling mirror, with the cavity having a plurality of optical resonance cavity modes, and a laser that emits continuous wave laser light, wherein the laser is capable of being scanned whereby a mean optical frequency of the laser is adjustable over a range of frequencies, and wherein the laser is responsive to optical feedback light emerging from the cavity. The system also typically includes mode matching optics configured to couple the laser light to the cavity via the cavity coupling mirror, and a detector configured to measure an intensity of the intracavity optical power of light circulating in the cavity and to generate a signal representing the intracavity optical power of light circulating in the cavity. In one embodiment, the transmissivity of a laser output coupler is selected such that the intensity of the optical feedback light impinging on the laser or the active laser medium is below a threshold intensity value so as to ensure locking to one or more of the plurality of optical resonance cavity modes that have a frequency within said range of frequencies of the laser.

According to still a further aspect, a system is provided for detecting one or more analyte species present in a gaseous or liquid medium. The system typically includes a resonant optical cavity containing the medium and having at least two cavity mirrors, one of which is a cavity coupling mirror, with the cavity having a plurality of optical resonance cavity modes, wherein the cavity has two sets of linearly polarized cavity modes orthogonal to each other, and a laser that emits continuous wave laser light, wherein the laser has a linearly polarized output, wherein the laser is capable of being scanned whereby a mean optical frequency of the laser is adjustable over a range of frequencies, and wherein the laser is responsive to optical feedback light emerging from the cavity. The system also typically includes mode matching optics configured to couple the laser light to the cavity via the cavity coupling mirror; and a detector configured to measure an intensity of the intracavity optical power of light circulating in the cavity and to generate a signal representing the intracavity optical power of light circulating in the cavity. In one embodiment, the intensity of the optical feedback light impinging on the laser is controlled to be below a threshold intensity value that ensures locking to one or more of the plurality of optical resonance cavity modes that have a frequency within said range of frequencies of the laser by selection of an orientation of the laser relative to the cavity so that the output polarization of the laser makes a non-zero angle with respect to the polarization of the cavity modes and/or by selection of the reflectivities of the at least two cavity mirrors.

In certain aspects, the laser includes a semiconductor diode laser. In certain aspects, the optical feedback light impinges on the laser from the cavity coupling mirror. In certain aspects, the reflectivity of the cavity coupling mirror is greater than the reflectivity of the other cavity mirror(s).

In the various embodiments, as the mean optical frequency of the laser is sequentially adjusted (scanned) over the range of frequencies, the laser advantageously locks to sequential cavity modes without missing any cavity modes. The laser can also be reproducibly locked to any optical resonance cavity mode within the adjustable frequency range of the laser.

In certain aspects, the cavities of the various embodiments can have a structure of a ring cavity having three or more cavity mirrors, a linear cavity having two cavity mirrors, or a V-shaped cavity having three cavity mirrors.

In certain aspects for the various embodiments, a means for adjusting a phase of the optical feedback light is provided. In certain aspects for the various embodiments, a means for adjusting the intensity of the optical feedback light is provided. Such means may include, for example, an optical attenuator element positioned between the laser and the cavity along a path of the optical feedback light.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

BRIEF DESCRIPTION OF THE DRAWINGS

FIG. 5 illustrates a cavity enhanced absorption spectroscopy (CEAS) system according to yet another embodiment.

DETAILED DESCRIPTION

The present invention provides cavity enhanced absorption spectroscopy systems and methods for measuring trace gases with improved scan to scan mode coupling efficiency and improved optical feedback control.

Embodiments of the present invention provide simple, precise and reliable cavity enhanced absorption spectroscopy systems and methods for detecting trace gases that have improved accuracy and stability as compared to existing systems and methods based upon similar principles. This is achieved, in part, by excluding from the optical path between the laser and the cavity components that may cause optical interference effects, temperature, and/or ageing drifts, etc., and adding to or enhancing features of the remaining components to provide improved device operation in the absence of the removed components. For example, embodiments of CEAS systems as disclosed herein advantageously do not require or need any settable attenuator, e.g., placed in the path between the laser and the cavity, or other element to attenuate or control the laser-cavity coupling rate.

Figure 1:
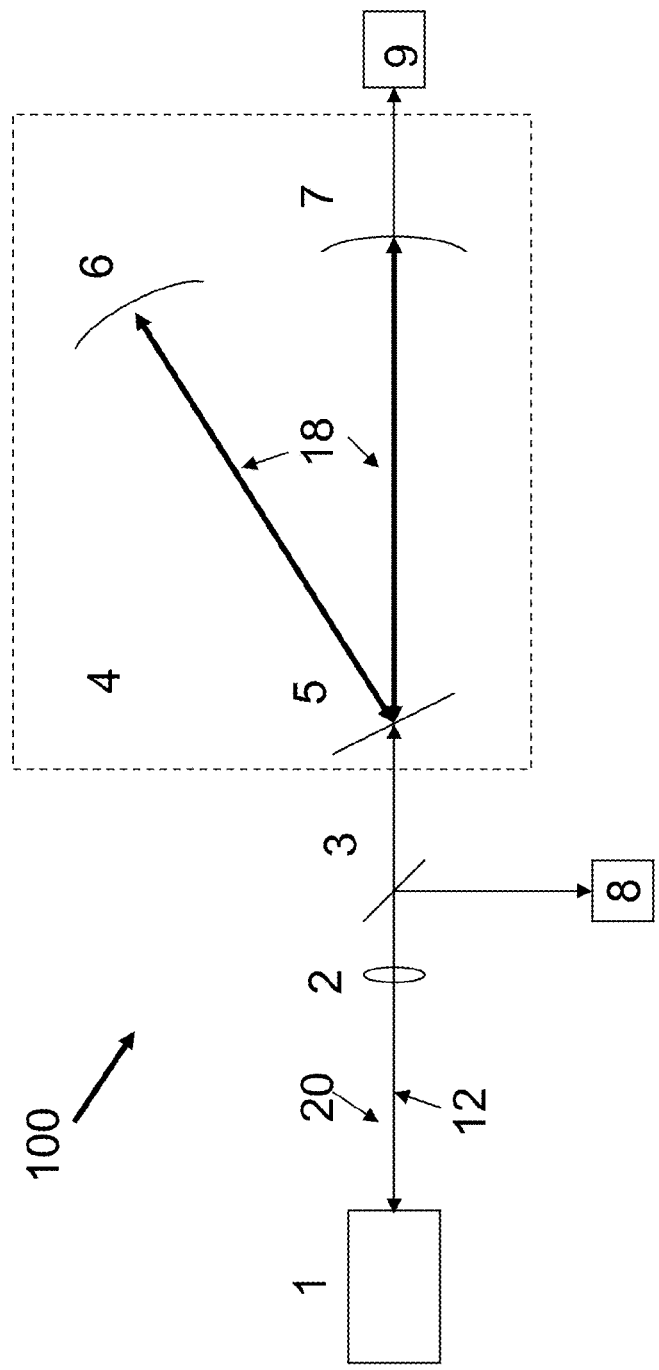
FIG. 1 illustrates a cavity enhanced absorption spectroscopy (CEAS) system according to one embodiment.

FIG. 1 illustrates a cavity enhanced absorption spectroscopy (CEAS) system 100 according to one embodiment. As shown, CEAS system 100 includes a light source 1 that emits continuous wave coherent light, such as continuous wave laser light, an optical cavity 4 and two detectors, detector 8 and detector 9. As shown, cavity 4 is a V-shaped cavity defined by cavity coupling mirror 5 and mirrors 6 and 7. It should be appreciated that the cavity could be a linear cavity with two or more mirrors, or a ring shaped cavity with three or more mirrors, or any other structure having three or more mirrors. An enclosure or housing (not shown) provides an air tight seal for cavity 4 such as to allow control of the environment within the housing and hence the cavity 4. One or more optical components 2 are configured and arranged to facilitate directing laser light from source 1 to the optical cavity 4 via cavity coupling mirror 5 and to ensure the mode matching of the laser to the cavity. In the embodiment shown in FIG. 1, a beam splitting element 3 is positioned and aligned so as to allow substantially all of the incident light 12 emitted or generated by source 1 to impinge on cavity coupling mirror 5. A portion of the incident light beam 12 is directed (e.g., reflected or refracted) by element 3 to detector 8. Cavity coupling mirror 5, in this embodiment, is arranged at an angle with respect to beam 12, although it could be perpendicular to beam 12. A portion of incident light 12 enters cavity 4 via mirror 5. Depending on the frequency of incident light 12 and the optical length of cavity 4 (e.g., optical length from mirror 7 to mirror 5 to mirror 6) light 18 circulating in the cavity may build up and resonate at one or a plurality of cavity modes defined by the optical length of the cavity. A portion of the intra-cavity light 18 circulating in cavity 4 between mirrors 7, 5 and 6, emerges or escapes via mirror 5 and impinges on element 3. Element 3 allows a portion 20 to pass back to source 1.

In certain aspects, source 1 includes a laser or other coherent light source that is sensitive or responsive to optical feedback. One useful laser is a semiconductor diode laser that is sensitive to optical feedback from light 20 impinging on the laser from the cavity, e.g., from coupling mirror 5 in the current configuration. In general, useful laser sources might include diode lasers, quantum cascade lasers and solid state lasers, any external cavity laser, etc. Selection of the reflectivities (or transmissivities) of mirrors 5, 6 and 7 defines the intensity of beam 20 and hence the optical feedback intensity (see e.g., FIG. 4) provided to laser 501. By setting or controlling the optical feedback intensity, the laser can be coupled to any cavity mode which is in the laser scanning range.

Source 1 is also preferably capable of being frequency scanned, whereby a mean optical frequency of the laser is adjustable over a range of frequencies. This can be accomplished as is well known, such as, for example, by adjusting the current applied to a diode laser and/or adjusting a temperature of the laser medium. In certain aspects, the cavity 4 is also capable of being frequency scanned, e.g., by changing or adjusting an optical length of the cavity, whereby an optical frequency of a cavity resonance peak is adjustable over a range of frequencies. Adjustment of the optical length of the cavity can include adjusting or modulating a relative position of one or more of the cavity mirrors, adjusting a pressure of the medium within cavity 4 or other ways as are known to one skilled in the art.

In certain embodiments, CEAS system 10 is useful for detecting trace gases within a gas mixture present in the cavity 4. When the frequency of the light 12 emitted by source 1 approaches the frequency of one of the cavity modes, the light 12 entering the cavity 4 begins to fill the cavity to that mode. The optical intensity of the light 18 circulating inside the resonance cavity reflects total cavity loss at the moment when the light frequency of light 12 coincides with the cavity mode transmission peak. The total cavity loss is a sum of the cavity mirror losses and losses caused by absorption by one or more components of the gas mixture present in the cavity. Analyte absorption, e.g., absorption losses caused by absorption by the one or more gas components, is determined based on the difference of the cavity loss when the absorbing component is present in an analyzed gas and the cavity loss when the absorbing component is absent in a reference gas.

Figure 2:
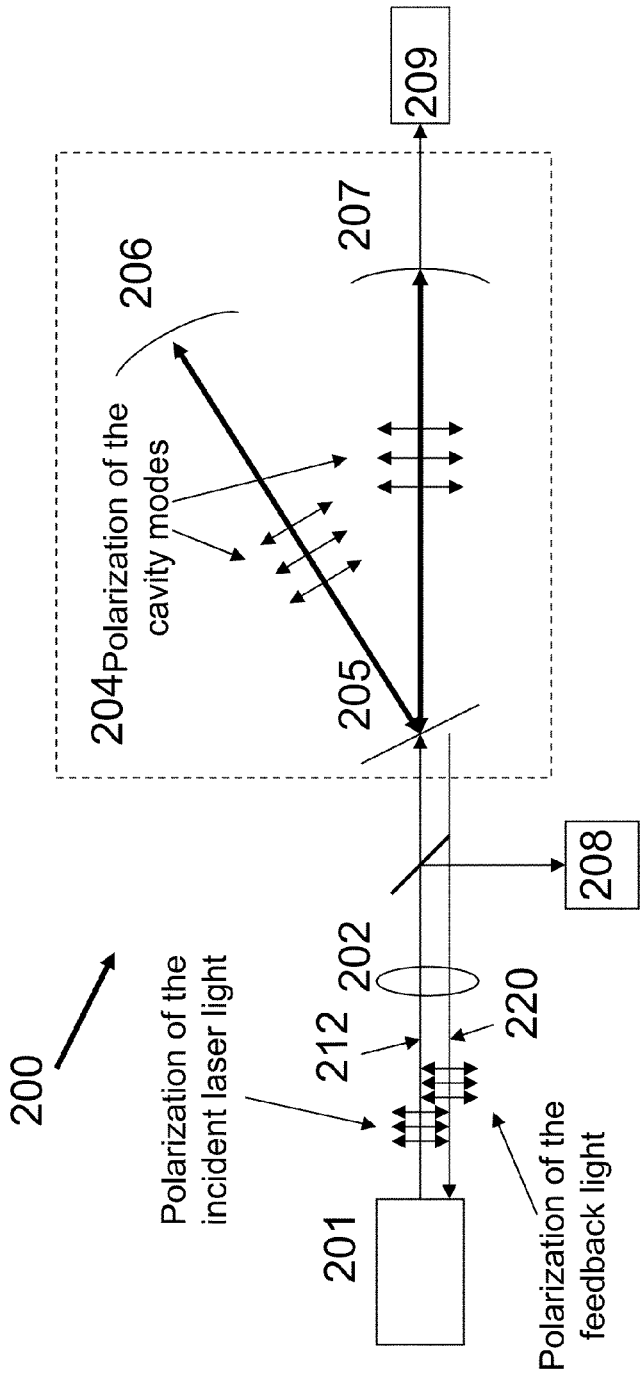
FIGS. 2 and 3 illustrate a cavity enhanced absorption spectroscopy (CEAS) system 200 wherein selection or adjustment of polarization orientation is used to control the intensity of the optical feedback to the laser source according to another embodiment.
Figure 3:
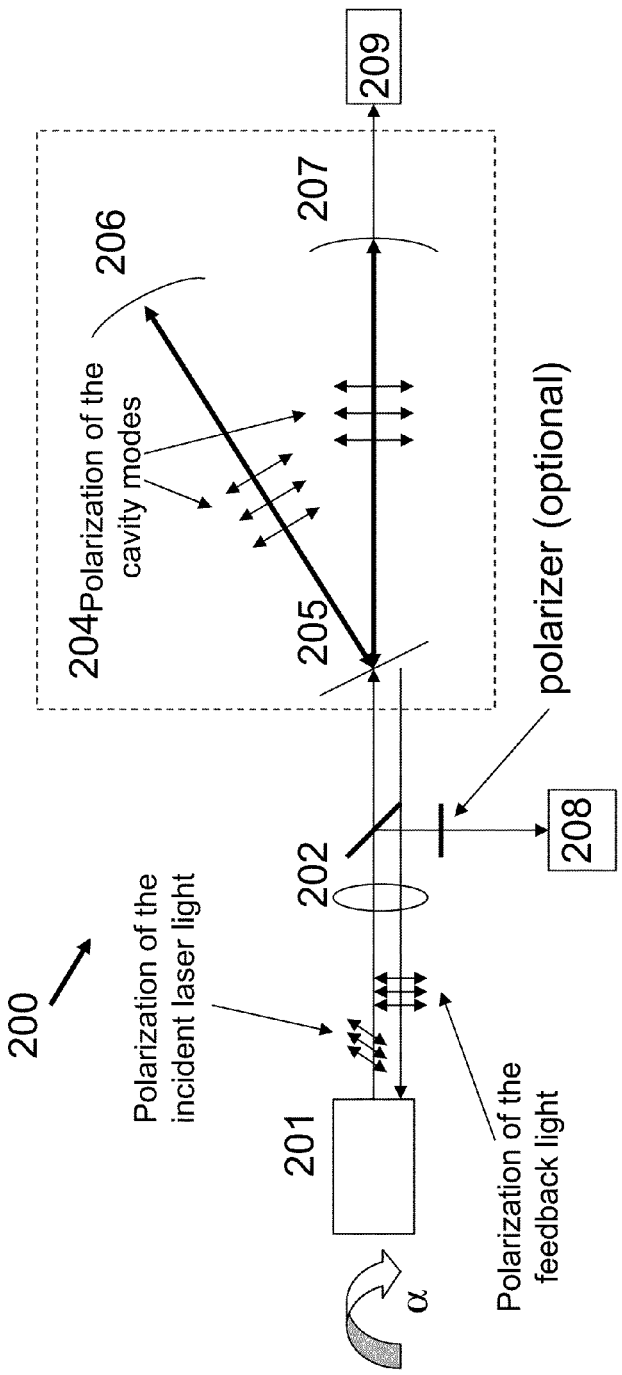

FIGS. 2 and 3 illustrates a cavity enhanced absorption spectroscopy (CEAS) system 200 wherein selection or adjustment of polarization orientation is used to control the intensity of the optical feedback to the laser source according to another embodiment. The principle of operation of CEAS system 200 is similar to that of CEAS system 100, including operation of a v-shaped cavity structure 204, with cavity mirror 205 being a cavity coupling mirror. Here, as shown the source 201 has an intrinsic linearly polarized emission and the cavity has two sets of linearly polarized modes orthogonal to each other. In FIG. 2, the polarization of the incident laser beam 212 coincides with the polarization of the cavity mode. In FIG. 3 the polarization of the incident laser beam 212 does not coincide with the polarization of the cavity mode, and hence the intensity of the optical feedback to laser 201 is reduced. In this embodiment, a means to rotate the polarization of the incident laser light 212 is provided for use in setting, controlling or adjusting the optical feedback intensity to the laser 201. The means, in certain aspects, includes a mechanical element coupled with the laser, or a platform holding the laser, that physically rotates the laser so that the output polarization is rotated. For example, if the polarization vector of beam 212 is rotated by angle $\alpha$ relative to the polarization of the cavity mode, the intracavity power is proportional to $\cos(\alpha)$, and the intensity of the light 220 directed back to the laser 201 is also proportional to $\cos(\alpha)$, however, the intensity of the feedback light coupled to the laser mode is proportional to $\cos^2(\alpha)$. It should be noted that no attenuator between the cavity and laser need be used as the mutual orientation of the cavity and the laser affects the cavity coupling rate.

Figure 4:
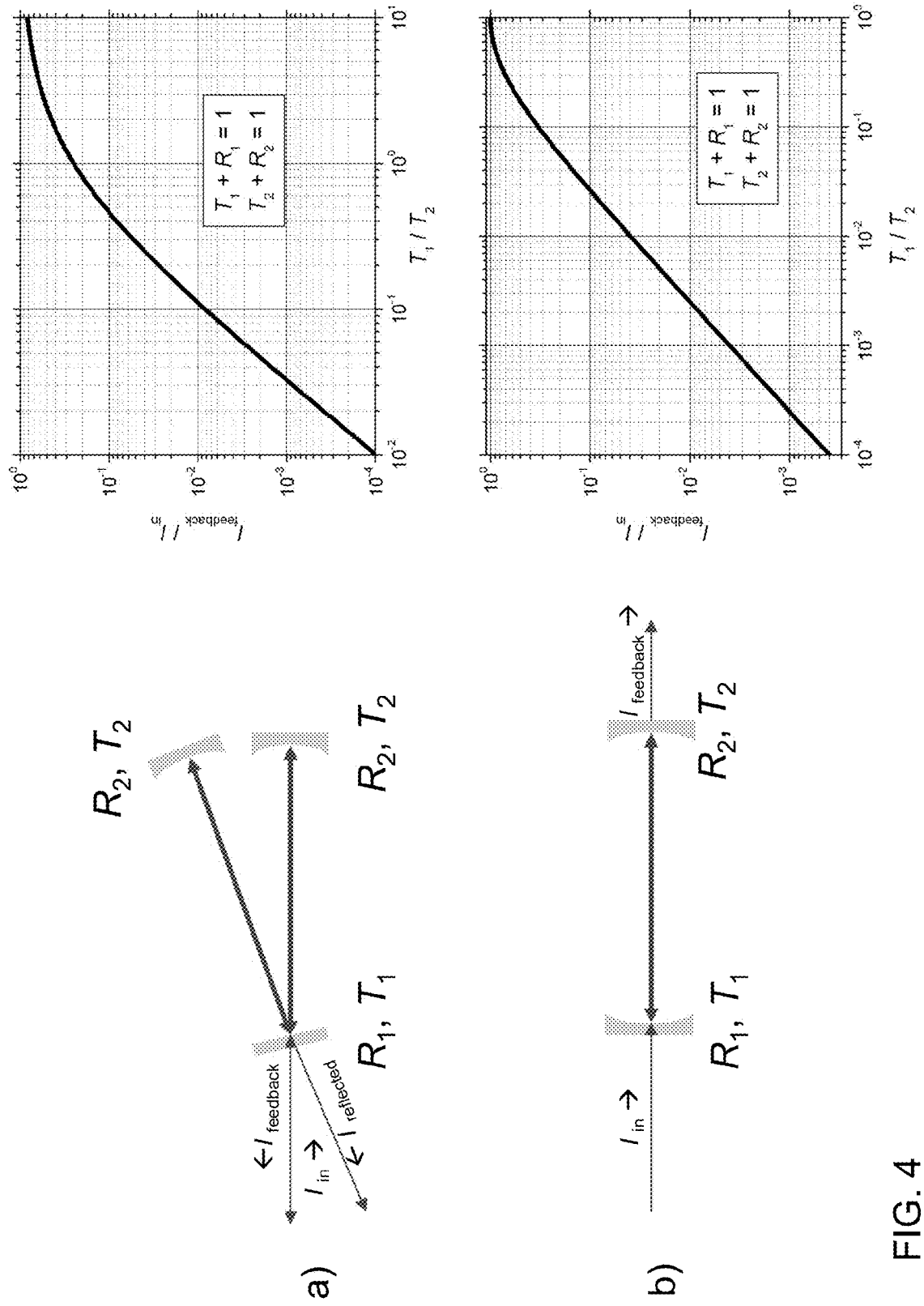
FIG. 4 illustrates the relationship of the reflectivities of the cavity mirrors for a v-shaped cavity that defines the intensity of the feedback to the laser source.

FIG. 4 shows the relationship of the intensity of the feedback to the laser source as a function of the reflectivities of the cavity mirrors for a v-shaped cavity (FIG. 4a) and for a linear cavity (FIG. 4b). For simplicity, any absorption losses on the mirrors in the cavity are neglected. Generally, it is desirable that the reflectivity (R) of the cavity coupling mirror be greater than, or even significantly greater than, the reflectivities (R1) of the other mirror(s) of the cavity. Or, said another way, it is desirable that the transmissivity (T=1−R) of the cavity coupling mirror be less than, or even significantly less than, the transmissivities (T1) of the other mirror(s) of the cavity. FIG. 4. also shows two configurations: a) in which the mirror, from which the feedback light emerges from the cavity, is the same as an input mirror (FIG. 4a); and b) where the input and output mirrors are different. The second configuration where the input and feedback mirrors are different is advantageous for OFCEAS and PAS applications as such configuration typically provides for a greater intracavity power. Useful configurations for controlling and steering the output/feedback beam are discussed below with reference to FIG. 7.

FIG. 5 illustrates a cavity enhanced absorption spectroscopy (CEAS) system 500 according to yet another embodiment. The principle of operation of CEAS system 500 is similar to that of CEAS system 100, including a v-shaped cavity structure 504, with cavity mirror 505 being a cavity coupling mirror. Cavity coupling mirror 505, in this configuration, is positioned and oriented such that incident light beam 512 generated by source 501 impinges upon mirror 505 at an angle relative to the plane defined by mirror 505 at the area of impact. The mirror 505 could be oriented perpendicular to beam 512. Detector 509 detects light emerging from mirror 507 and generates a signal representing the intracavity optical power of light circulating in the cavity 504. An intelligence module (not shown) receives and processes the detector output signals. Here, laser output coupler 503 of laser 501, has its transmissivity set, or adjusted, so as to control the intensity of feedback light interacting with laser 501, or laser medium 522, e.g., to provide optical feedback intensity below a threshold value. Laser 501 includes any laser having an output coupler, e.g., an external cavity laser.

Figure 6:
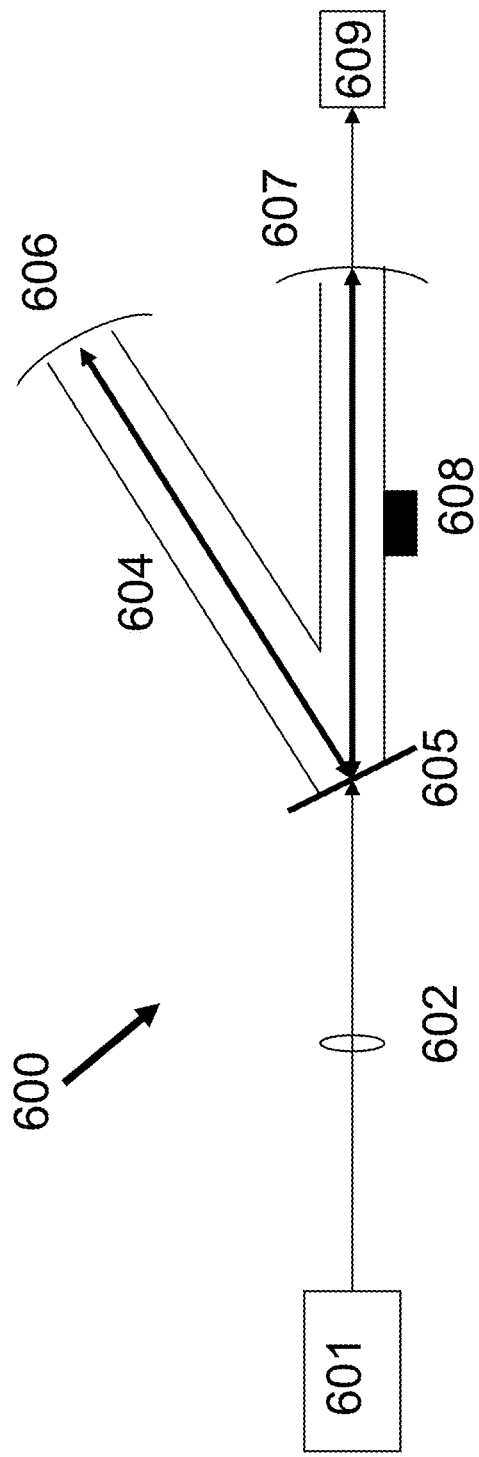
FIG. 6 illustrates a cavity enhanced absorption spectroscopy (CEAS) system according to yet a further embodiment.

FIG. 6 illustrates a cavity enhanced absorption spectroscopy (CEAS) system 600 according to yet a further embodiment that allows for both photo-acoustic spectroscopy (PAS) and direct absorption spectroscopy measurements using the same cavity. The principle of operation of CEAS system 600 is similar to that of CEAS system 100, including a v-shaped cavity structure 604, with cavity mirror 605 being a cavity coupling mirror. Cavity coupling mirror 605 is positioned such that incident light beam 612 generated by source 601 impinges upon mirror 605 at an angle relative to the plane defined by mirror 605 at the area of impact. The mirror 605 could be oriented perpendicular to beam 612. Detector 609 detects light emerging from mirror 607 and generates a signal representing the intracavity optical power of light circulating in the cavity 604. Detector 608, in this embodiment, is positioned internal to the cavity (e.g., within the cavity housing structure) to detect a response of the gas mixture filling the optical cavity 604 to the intracavity optical power in the form of an acoustic signal. U.S. patent application Ser. No. 12/660,614, filed on Mar. 2, 2010, provides details of photo-acoustic spectroscopy, useful photo-acoustic sensors and photo-acoustic measurement techniques and parameters, the contents of which are hereby incorporated by reference in its entirety. An intelligence module (not shown) receives and processes the detector output signals, and provides output signals representative of the PAS and/or CEAS measurements.

Figure 7:
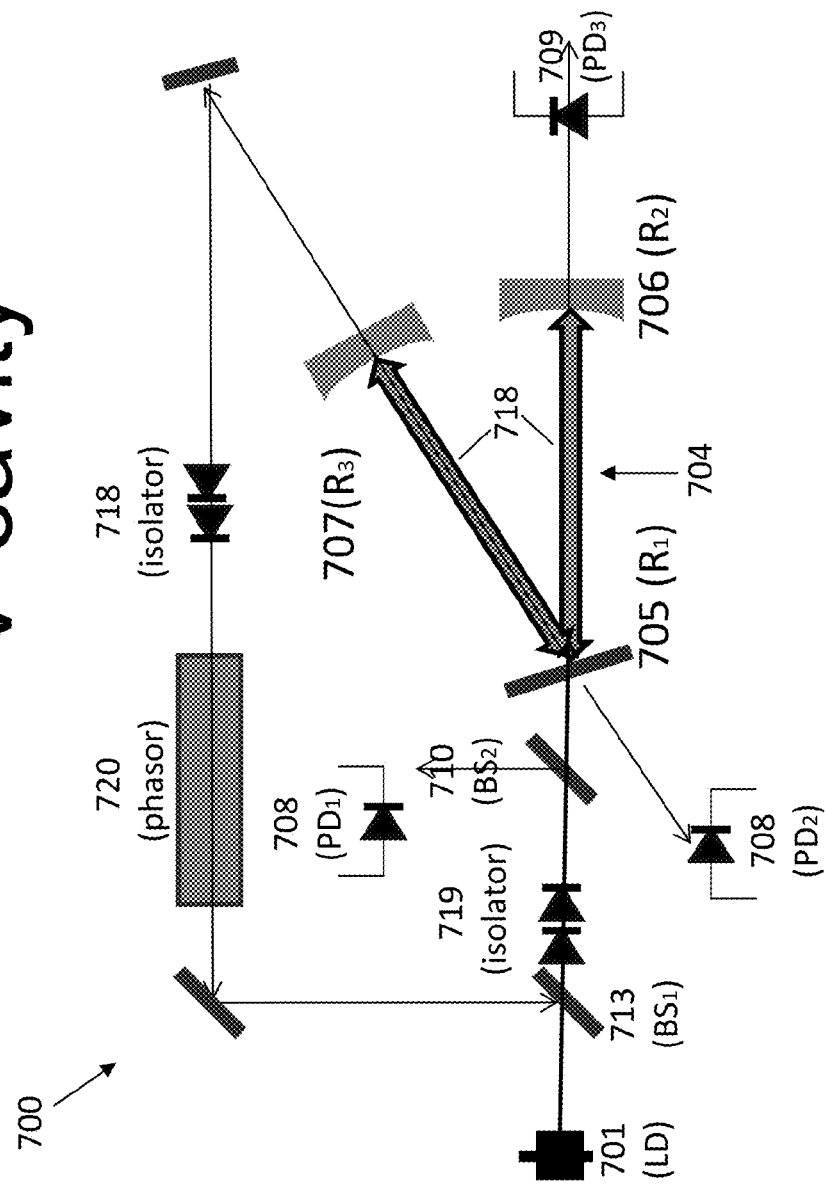
FIG. 7 illustrates a CEAS system having a v-shaped cavity configuration according to another embodiment.

In certain embodiments, a means for organizing an unidirectional beam path around the optical cavity is provided. For example, such an arrangement might include one or more optical isolators, which prevent light propagation from the cavity to the laser in opposite direction. In certain embodiments, a means for adjusting the intensity of the optical feedback light is provided. For example, FIG. 7 illustrates a cavity enhanced absorption spectroscopy (CEAS) system 700 according to such an embodiment. The principle of operation of CEAS system 700 is similar to that of CEAS system 100, for example, including a v-shaped cavity structure 704, with cavity mirror 705 being a cavity coupling mirror. Cavity coupling mirror 705 is positioned such that incident light beam 712 generated by laser diode source 701 impinges upon mirror 705 at an angle relative to the plane defined by mirror 705 at the area of impact so that light is reflected to photodetector 708. Optional beamsplitting element 703 directs a portion of incident beam 712 to optional detector 710. Photodetector 709, in this embodiment, is positioned to receive and detect the portion of the intra-cavity light 718 circulating back and forth within cavity 704 between mirrors 705, 706 and 707 that emerges or escapes via mirror 706. Similar to the operation of CEAS 100, photodetector 710 detects and generates a signal representing the intensity of the laser light 712 incident on the cavity coupling mirror 705, detector 708 detects and generates a signal representing the intensity of the laser light reflected by the cavity coupling mirror 705, and detector 709 detects and generates a signal representing the intracavity optical power of light circulating in the cavity 704. An intelligence module (not shown) receives the three detector output signals and processes these signals to produce or generate output signal(s).

Also as shown in FIG. 7 are additional elements to enhance control of the optical feedback, specifically control of the optical feedback to source 701. As shown, light emerging from cavity mirror 707 passes through a phasor 720 and returns to source 701, via beamsplitting element 713. Optical isolators 718 and 719 are provided to completely block light which travels in the opposite direction. For example, optical isolator element 719 blocks light returning (e.g., reflected light or light escaping from the cavity via mirror 705) from mirror 705 toward source 701, and optical isolator element 718 prevents light returning from phasor 720 (e.g., light reflected by phasor 720 or source light reflected by beamsplitter 713 that is passing through phasor 720 on an opposite path) from impinging on mirror 707. Selection of the cavity mirror reflectivities (e.g., R1, R2 and R3) defines the optical feedback intensity provided to source 701. Use of phasor 720 advantageously allows for phase control of the optical feedback provided to source 701 from the cavity 704. It should be appreciated that similar structures and/or functionality for guiding a beam and controlling feedback intensity can be applied to linear cavities and ring cavities.

As used herein, the terms "threshold intensity value" or "threshold value" when used with reference to optical feedback of the laser source is intended to mean the intensity of the optical feedback above which the laser will lock to a cavity mode for one FSR (free spectral range) of the cavity. Two examples show the condition when the optical feedback strength is above the threshold value: 1) when a cavity mode is scanned for more than one FSR, but the laser continues to be locked to the same cavity mode; 2) when the laser current or temperature of the laser is adjusted so that the laser frequency is scanned, and when unperturbed by optical feedback the laser frequency would be scanned for more than one cavity FSR, whereas in the presence of the (high) optical feedback the laser continues to be locked to the same cavity mode. As above, it is desirable in cavity enhanced absorption systems and methods to avoid this situation, and indeed the above embodiments advantageously ensure that the laser locks to sequential cavity modes as the laser wavelength is being scanned without missing any cavity modes.

While the invention has been described by way of example and in terms of the specific embodiments, it is to be understood that the invention is not limited to the disclosed embodiments. To the contrary, it is intended to cover various modifications and similar arrangements as would be apparent to those skilled in the art. Therefore, the scope of the appended claims should be accorded the broadest interpretation so as to encompass all such modifications and similar arrangements.

What is claimed is:

1. A system for detecting one or more analyte species present in a gaseous or liquid medium, the system comprising:
   a resonant optical cavity containing said medium and having at least two cavity mirrors, one of which is a cavity coupling mirror, the cavity having a plurality of optical resonance cavity modes;
   a laser that emits continuous wave laser light, wherein the laser is capable of being scanned whereby a mean optical frequency of the laser is adjustable over a range of frequencies, and wherein the laser is responsive to optical feedback light emerging from the cavity;
   mode matching optics configured to couple the laser light to the cavity via the cavity coupling mirror; and
   a detector configured to measure an intensity of the intracavity optical power of light circulating in the cavity and to generate a signal representing the intracavity optical power of light circulating in the cavity
   wherein the transmissivity of at least one of the cavity mirrors is selected such that the intensity of the optical feedback light impinging on the laser is below a threshold intensity value so as to ensure that a frequency hold interval range of the optical frequency of the laser is smaller than a free spectral range of the cavity.

2. The system of claim 1, wherein the cavity has a configuration selected from the group consisting of a ring cavity having three or more cavity mirrors, a linear cavity having two or more cavity mirrors, and a V-shaped cavity having three cavity mirrors.

3. The system of claim 1, further including an acoustic sensor incorporated inside the optical cavity to measure a photo-acoustic signal generated by the gaseous or liquid medium within the cavity.

4. The system of claim 1, further including a means for adjusting the mean optical frequency of the laser so as to scan the mean optical frequency of the laser over a cavity resonance peak.

5. The system of claim 1, wherein the cavity is capable of being scanned whereby an optical frequency of a cavity resonance mode peak is adjustable over a range of frequencies.

6. The system of claim 5, further including a means for controlling a position of one of the cavity mirrors so as to scan the optical frequency of the cavity resonance mode peak.

7. The system of claim 1, wherein the laser has a linearly polarized output and wherein the cavity has two sets of linearly polarized modes orthogonal to each other.

8. The system of claim 7, wherein an orientation of the laser relative to the cavity is adjustable so that the output polarization of the laser makes a non-zero angle with respect to the polarization of the cavity modes so that the intensity of the optical feedback light impinging on the laser is below the threshold intensity value.

9. The system of claim 8, wherein the non-zero angle is selected so as to provide optical feedback intensity for each set of modes below the threshold value.

10. The system of claim 1, wherein as the mean optical frequency of the laser is sequentially adjusted (scanned) over the range of frequencies, the laser locks to sequential cavity modes.

11. A system for detecting one or more analyte species present in a gaseous or liquid medium, the system comprising:
a resonant optical cavity containing said medium and having at least two cavity mirrors, one of which is a cavity coupling mirror, the cavity having a plurality of optical resonance cavity modes, wherein the cavity has two sets of linearly polarized cavity modes orthogonal to each other;
a laser that emits continuous wave laser light, wherein the laser has a linearly polarized output, wherein the laser is capable of being scanned whereby a mean optical frequency of the laser is adjustable over a range of frequencies, and wherein the laser is responsive to optical feedback light emerging from the cavity;
mode matching optics configured to couple the laser light to the cavity via the cavity coupling mirror; and
a detector configured to measure an intensity of the intracavity optical power of light circulating in the cavity and to generate a signal representing the intracavity optical power of light circulating in the cavity
wherein an orientation of the laser relative to the cavity is selected so that the output polarization of the laser makes a non-zero angle with respect to the polarization of the cavity modes so that the intensity of the optical feedback light impinging on the laser is below a threshold intensity value so as to ensure that a frequency hold interval range of the optical frequency of the laser is smaller than a free spectral range of the cavity.

12. The system of claim 11, wherein the cavity has a configuration selected from the group consisting of a ring cavity having three or more cavity mirrors, a linear cavity having two or more cavity mirrors, and a V-shaped cavity having three cavity mirrors.

13. The system of claim 11, further including a first detector configured to measure an intensity of the intracavity optical power of light circulating in the cavity and to generate a signal representing the intracavity optical power of light circulating in the cavity.

14. The system of claim 11, further including a means for adjusting the mean optical frequency of the laser so as to scan the mean optical frequency of the laser over a cavity resonance peak.

15. The system of claim 11, wherein the cavity is capable of being scanned whereby an optical frequency of a cavity resonance peak is adjustable over a range of frequencies.

16. The system of claim 11, wherein as the mean optical frequency of the laser is sequentially adjusted (scanned) over the range of frequencies, the laser locks to sequential cavity modes.

17. The system of claim 11, wherein the orientation of the laser relative to the cavity is adjustable so that the output polarization of the laser makes a non-zero angle with respect to the polarization of the cavity modes so that the intensity of the optical feedback light impinging on the laser is below the threshold intensity value.

18. The system of claim 17, wherein the non-zero angle is selected so as to provide optical feedback intensity for each set of modes below the threshold value.

19. The system of claim 11, further including an acoustic sensor incorporated inside the optical cavity to measure a photo-acoustic signal generated by the gaseous or liquid medium within the cavity.

20. A system for detecting one or more analyte species present in a gaseous or liquid medium, the system comprising:
a resonant optical cavity containing said medium and having at least two cavity mirrors, one of which is a cavity coupling mirror, the cavity having a plurality of optical resonance cavity modes;
a laser that emits continuous wave laser light, wherein the laser is capable of being scanned whereby a mean optical frequency of the laser is adjustable over a range of frequencies, and wherein the laser is responsive to optical feedback light emerging from the cavity;
mode matching optics configured to couple the laser light to the cavity via the cavity coupling mirror; and
a detector configured to measure an intensity of the intracavity optical power of light circulating in the cavity and to generate a signal representing the intracavity optical power of light circulating in the cavity
wherein the transmissivity of a laser output coupler is selected such that intensity of the optical feedback light impinging on the laser is below a threshold intensity value so as to ensure that a frequency hold interval range of the optical frequency of the laser is smaller than a free spectral range of the cavity.

21. A method for detecting one or more analyte species present in a gaseous or liquid medium using a laser that that emits continuous wave laser light and a resonant optical cavity containing said medium and having at least two cavity mirrors, one of which is a cavity coupling mirror, wherein the laser is responsive to optical feedback light emerging from the cavity, and wherein a mean optical frequency of the laser is adjustable over a range of frequencies, the method comprising:
coupling the laser light to the cavity via the cavity coupling mirror using mode matching optics, the cavity having a plurality of optical resonance cavity modes;
adjusting a mean optical frequency of the laser so as to scan the mean optical frequency of the laser over one or more of the optical resonance cavity modes that have a frequency within said range of frequencies of the laser;
selecting the transmissivity of at least one of the cavity mirrors such that intensity of optical feedback light impinging on the laser is below a threshold intensity value so as to ensure that a frequency hold interval range of the optical frequency of the laser is smaller than a free spectral range of the cavity; and
measuring an intensity of the intracavity optical power of light circulating in the cavity and generating a signal representing the intracavity optical power of light circulating in the cavity.

22. The method of claim 21, wherein the cavity has a configuration selected from the group consisting of a ring cavity having three or more cavity mirrors, a linear cavity having two or more cavity mirrors, and a V-shaped cavity having three cavity mirrors.

23. The method of claim 21, wherein the laser has a linear polarized output and wherein the cavity has two sets of linearly polarized modes orthogonal to each other, the method further including adjusting an orientation of the laser relative to the cavity so that the output polarization of the laser makes a non-zero angle with respect to the polarization of the cavity modes.

24. A method for detecting one or more analyte species present in a gaseous or liquid medium using a laser that that emits continuous wave laser light and a resonant optical cavity containing said medium and having at least two cavity mirrors, one of which is a cavity coupling mirror, wherein the laser is responsive to optical feedback light emerging from the cavity, wherein the laser has a linear polarized output, and wherein a mean optical frequency of the laser is adjustable over a range of frequencies, the method comprising:

coupling the laser light to the cavity via the cavity coupling mirror using mode matching optics, wherein the cavity has a plurality of optical resonance cavity modes, and wherein the cavity has two sets of linearly polarized cavity modes orthogonal to each other;

adjusting a mean optical frequency of the laser so as to scan the mean optical frequency of the laser over one or more of the optical resonance cavity modes that have a frequency within said range of frequencies of the laser;

adjusting an orientation of the laser relative to the cavity so that the output polarization of the laser makes a non-zero angle with respect to the polarization of the cavity modes such that the intensity of optical feedback light impinging on the laser is below a threshold intensity value so as to ensure that a frequency hold interval range of the optical frequency of the laser is smaller than a free spectral range of the cavity; and measuring an intensity of the intracavity optical power of light circulating in the cavity and generating a signal representing the intracavity optical power of light circulating in the cavity.

25. The method of claim 24, wherein the cavity has a configuration selected from the group consisting of a ring cavity having three or more cavity mirrors, a linear cavity having two or more cavity mirrors, and a V-shaped cavity having three cavity mirrors.

26. The method of claim 24, wherein the non-zero angle is selected so as to provide optical feedback intensity for each set of cavity modes below the threshold value.

27. The system of claim 1, wherein as the mean optical frequency of the laser is scanned over said range of frequencies of the laser, sequential locking to the plurality of optical resonance cavity modes that have a frequency within said range of frequencies of the laser occurs.

28. The system of claim 11, further including a means for adjusting the intensity of the optical feedback light.

29. The system of claim 28, wherein the means for adjusting includes an optical attenuator element positioned between the laser and the cavity along a path of the optical feedback light.

30. The system of claim 1, further including a means for adjusting a phase of the optical feedback light.

* * * * *